United States Patent
del Nido et al.

(10) Patent No.: US 9,307,984 B2
(45) Date of Patent: Apr. 12, 2016

(54) TISSUE CLIP

(75) Inventors: Pedro J. del Nido, Boston, MA (US);
Nikolay Vasilyev, Boston, MA (US);
Franz Freudenthal, La Paz (BO)

(73) Assignee: Children's Medical Center Corporation, Boston, MA (US)

( * ) Notice: Subject to any disclaimer, the term of this patent is extended or adjusted under 35 U.S.C. 154(b) by 421 days.

(21) Appl. No.: 12/936,992

(22) PCT Filed: Apr. 16, 2009

(86) PCT No.: PCT/US2009/040769
§ 371 (c)(1),
(2), (4) Date: Oct. 8, 2010

(87) PCT Pub. No.: WO2009/129369
PCT Pub. Date: Oct. 22, 2009

(65) Prior Publication Data
US 2011/0054306 A1    Mar. 3, 2011

Related U.S. Application Data

(60) Provisional application No. 61/098,386, filed on Sep. 19, 2008, provisional application No. 61/045,303, filed on Apr. 16, 2008.

(51) Int. Cl.
*A61B 8/00* (2006.01)
*A61B 17/064* (2006.01)
*A61B 17/068* (2006.01)
(Continued)

(52) U.S. Cl.
CPC ......... *A61B 17/0644* (2013.01); *A61B 17/0682* (2013.01); *A61B 17/12109* (2013.01); *A61B 17/12172* (2013.01); *A61B 17/12022* (2013.01);
(Continued)

(58) Field of Classification Search
CPC .................................. A61B 8/12; A61N 7/02
USPC .................................. 600/439, 424
See application file for complete search history.

(56) References Cited

U.S. PATENT DOCUMENTS 7,087,066 B2 *   8/2006   Bolduc et al. ............. 606/153
7,338,506 B2     3/2008   Caro
(Continued)

OTHER PUBLICATIONS

International Search Report & Written Opinion, PCT/US2009/040769, mailed Jun. 12, 2009, 7 pages.
(Continued)

*Primary Examiner* — Tse Chen
*Assistant Examiner* — Hien Nguyen
(74) *Attorney, Agent, or Firm* — Fish & Richardson P.C.

(57) ABSTRACT

A tissue clip for adjoining tissues including a body portion, a biasing mechanism interconnecting the body portion to a tissue grasping mechanism, the grasping mechanism having a first condition wherein the grasping mechanism is extending against and away from the body portion and a second condition wherein the grasping mechanism is biased against the body portion. A tissue clip and deployer combination. A method of interconnecting tissue by deploying the tissue clip, puncturing tissue to be interconnected with the tissue clip, and interconnecting the tissue. A method of treating an aneurism by deploying the tissue clip at an aneurism site, closing off the aneurism site with the tissue clip, and treating the aneurism. A method of imaging a surgical procedure with ultrasound by modifying a surface of a metal surgical instrument, and imaging the metal surgical instrument with ultrasound during a surgical procedure.

29 Claims, 16 Drawing Sheets

(51) Int. Cl.
*A61B 17/12* (2006.01)
*A61B 17/00* (2006.01)
*A61B 17/11* (2006.01)
*A61B 19/00* (2006.01)

(52) U.S. Cl.
CPC ............... *A61B 2017/00243* (2013.01); *A61B 2017/1107* (2013.01); *A61B 2019/5425* (2013.01)

(56) References Cited

U.S. PATENT DOCUMENTS

| | | | |
|---|---|---|---|
| 2003/0032981 A1* | 2/2003 | Kanner et al. | 606/219 |
| 2004/0034297 A1 | 2/2004 | Darrow et al. | |
| 2004/0093023 A1* | 5/2004 | Allen et al. | 606/213 |
| 2005/0113767 A1* | 5/2005 | Palasis et al. | 604/264 |
| 2006/0135970 A1* | 6/2006 | Schaller | 606/152 |
| 2006/0190015 A1* | 8/2006 | Matsuno et al. | 606/142 |
| 2006/0293701 A1 | 12/2006 | Ainsworth et al. | |

OTHER PUBLICATIONS

Auto Suture Company, a Division of US. Surgical Corporation, "VCS Clip Applier System," published in 1995 (8 pages).

* cited by examiner

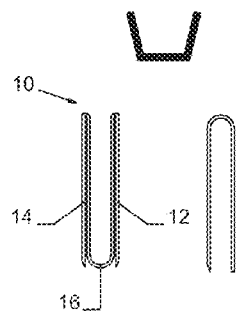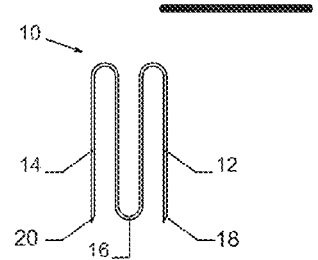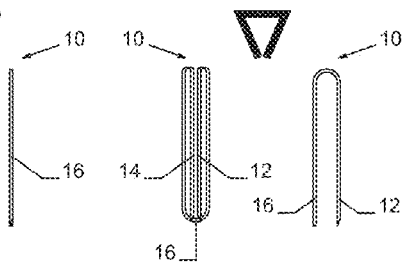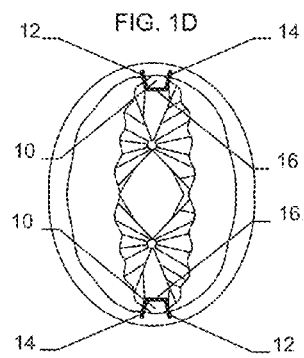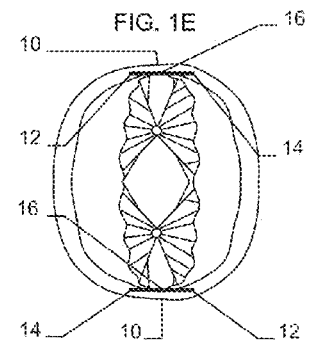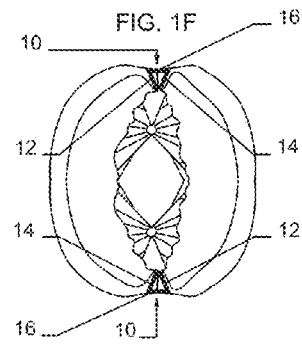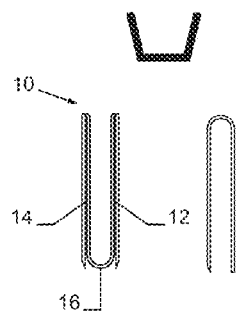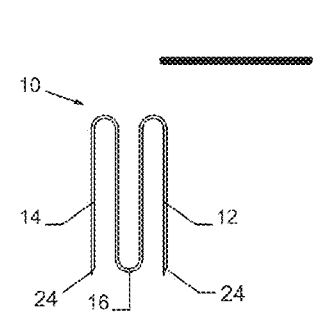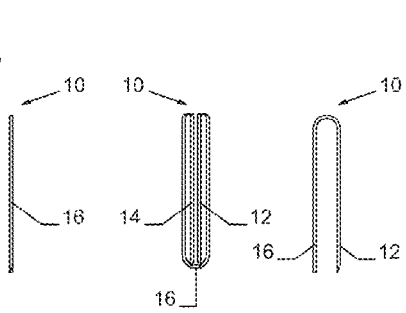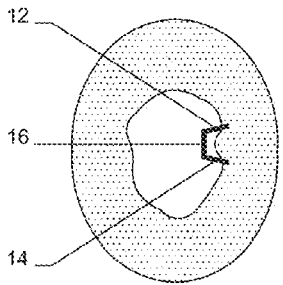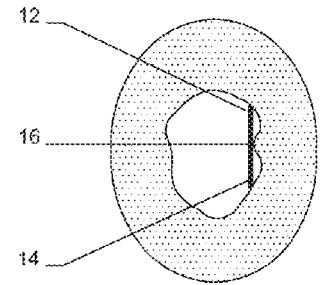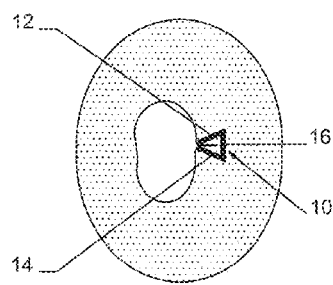

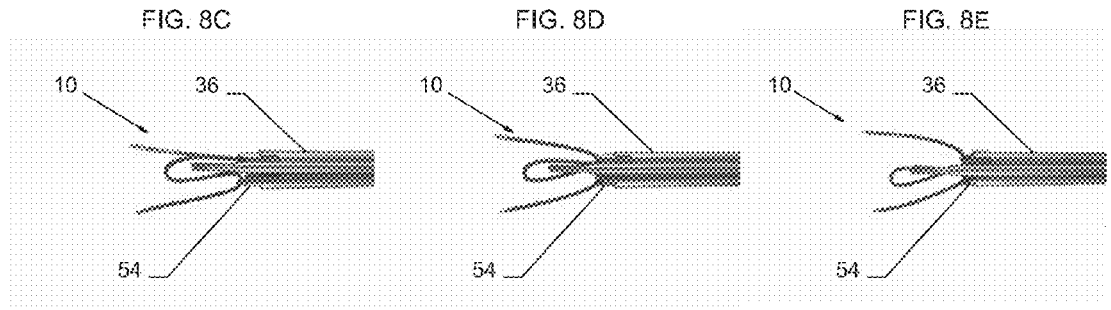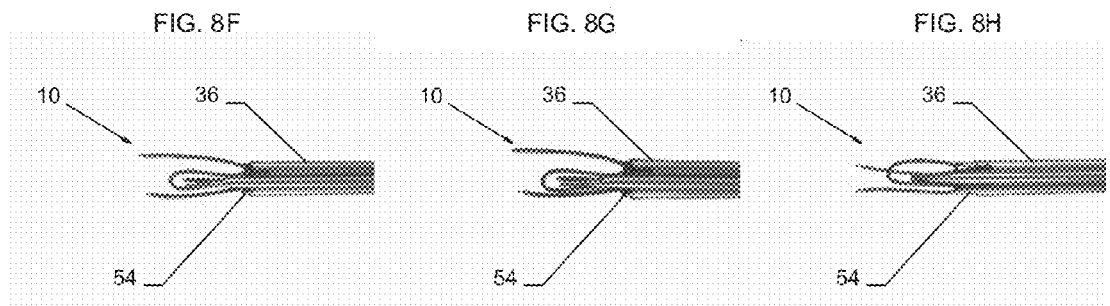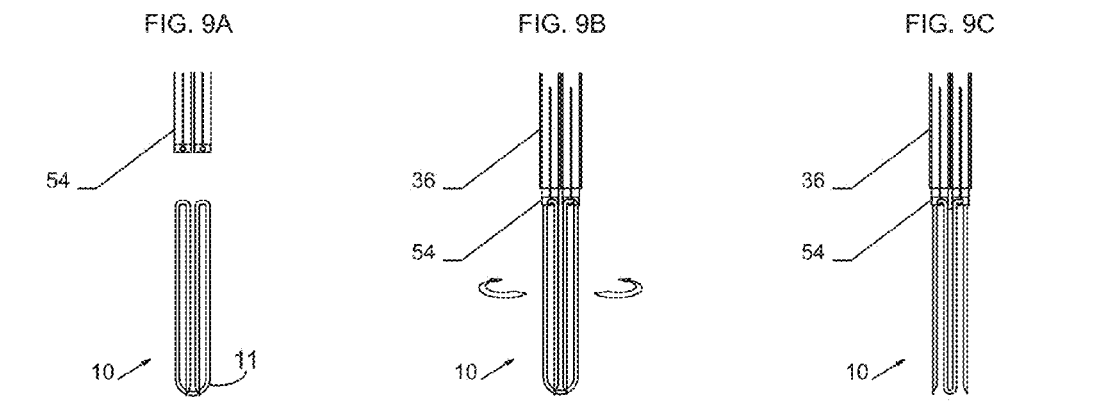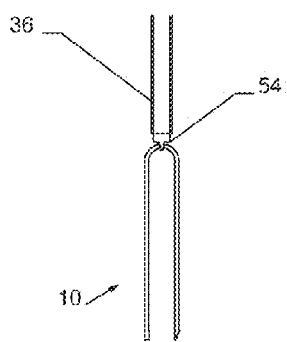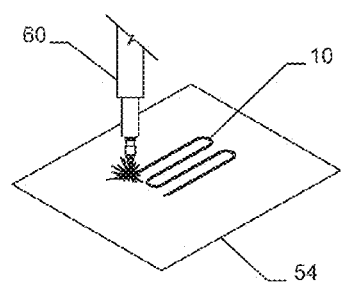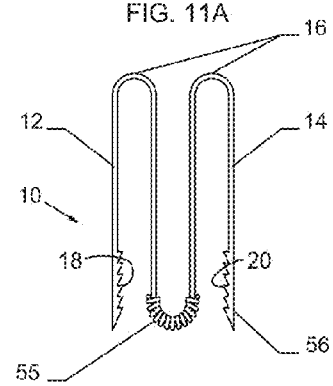

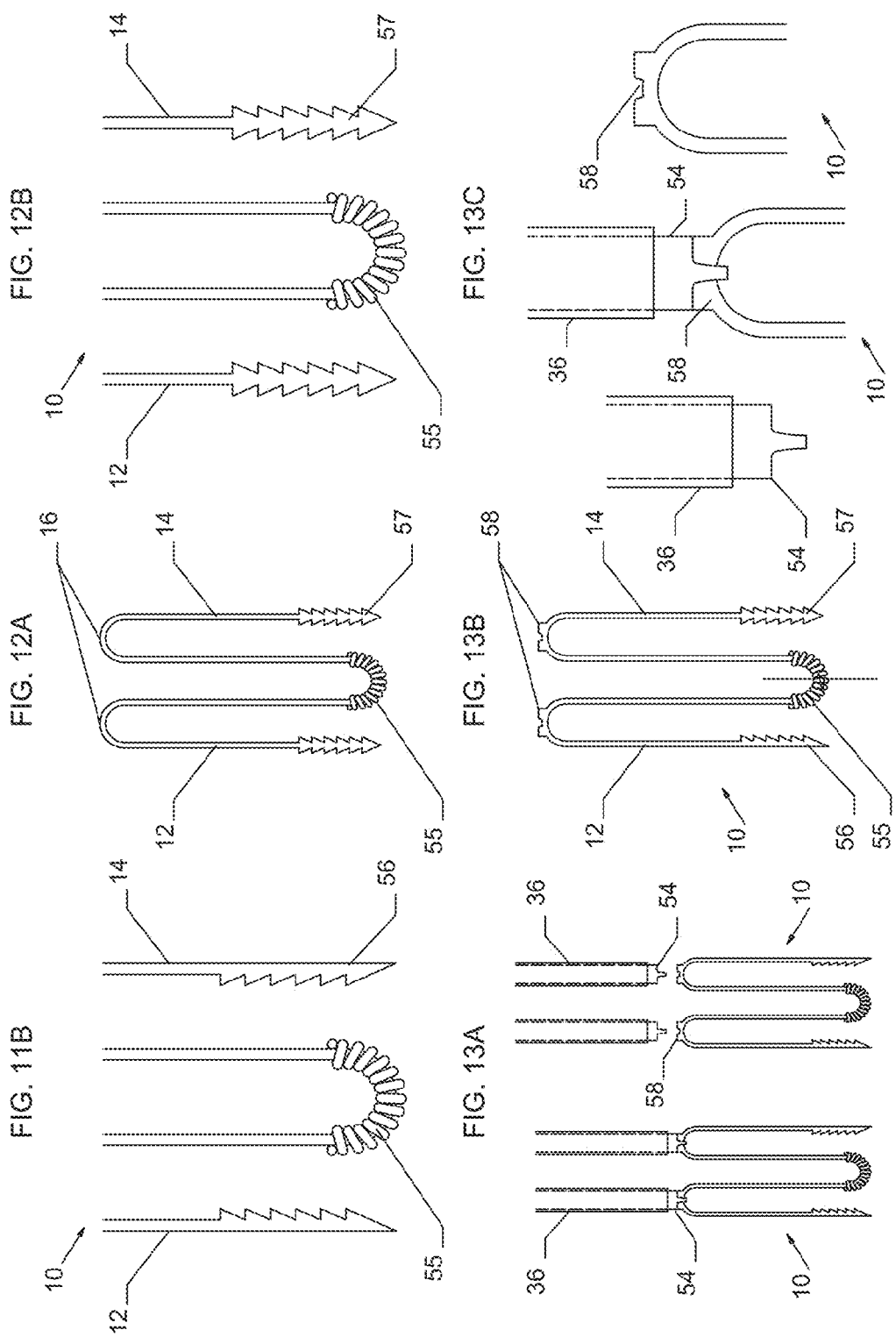

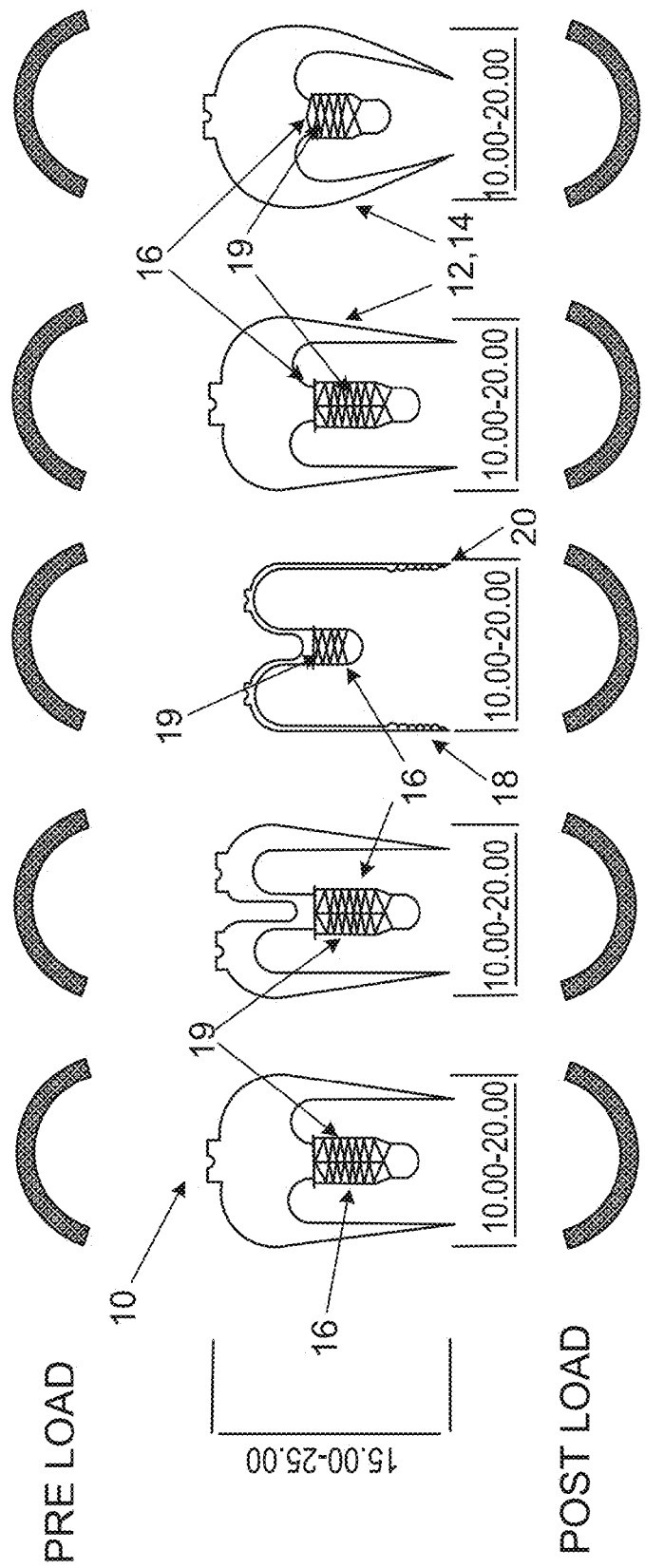

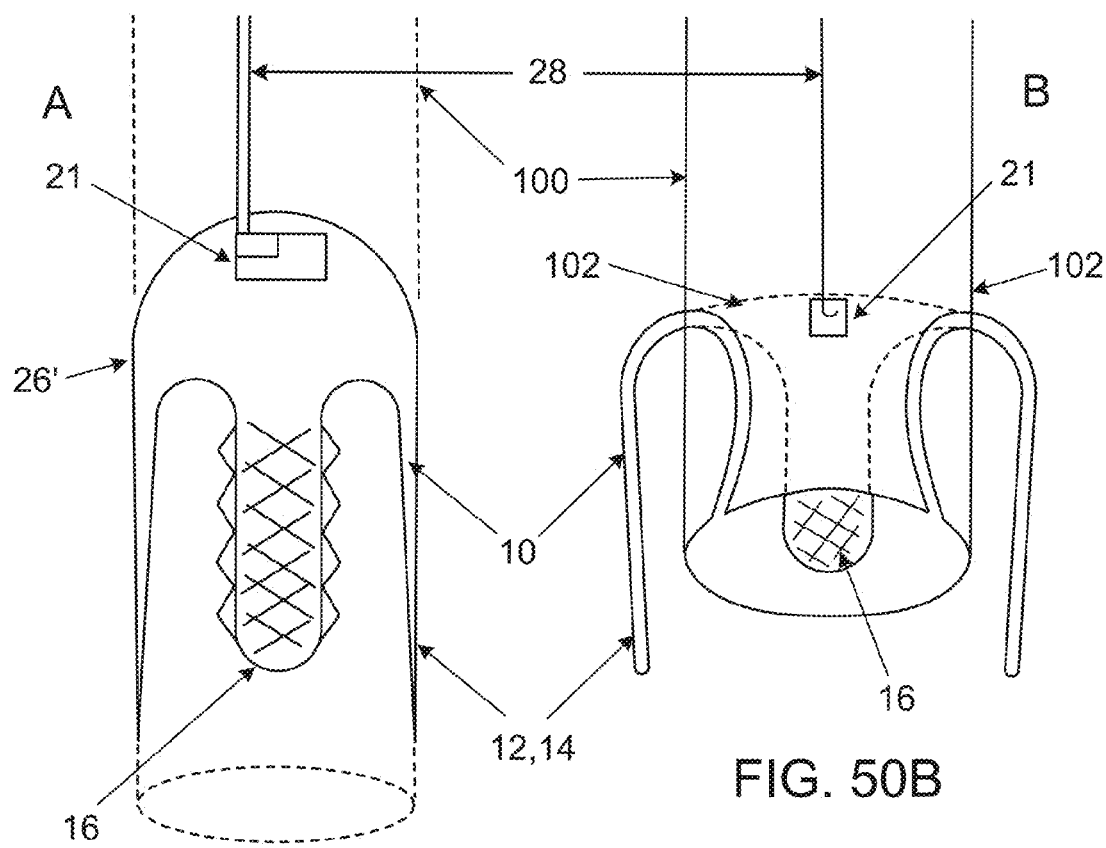
FIG. 50A
FIG. 50B
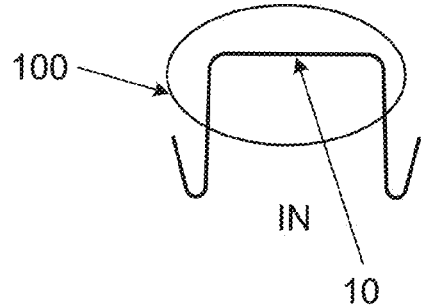
FIG. 50C
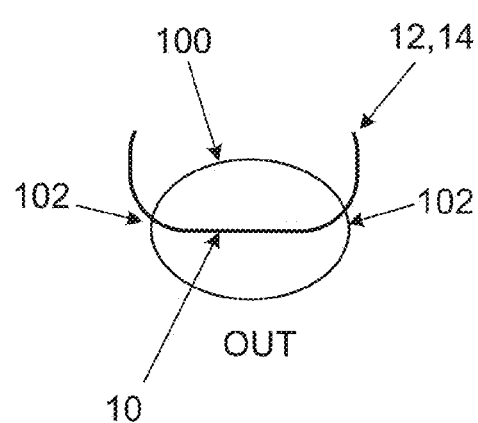
FIG. 50D

TISSUE CLIP

BACKGROUND OF THE INVENTION

1. Field of the Invention

Generally, the present invention relates to surgical devices. More specifically, the present invention relates to surgical devices for fastening tissues, closing tissues, and repairing tissues such as a mitral valve.

2. Description of Related Art

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trocar, which is a pointed, piercing device, is delivered into the body with a cannula. After the trocar pierces the abdominal or thoracic wall, it is removed and the cannula is left with one end in the body cavity, where the operation is to take place, and the other end opening to the outside. A cannula has a small inside diameter, generally 3-10 millimeters. A number of such cannulas are inserted for any given operation.

A viewing instrument, typically including a miniaturized video camera, is inserted through one of these cannulas and a variety of surgical instruments and retractors are inserted through others. The image provided by the viewing device may be displayed on a video screen or television monitor, affording the surgeon enhanced visual control over the instruments. Because a commonly used viewing instrument is called an "endoscope," this type of surgery is often referred to as "endoscopic surgery." In the abdomen, endoscopic procedures are commonly referred to as laparoscopic surgery, and in the chest, as thoracoscopic surgery. Abdominal procedures may take place either inside the abdominal cavity (in the intraperitoneal space) or in a space created behind the abdominal cavity (in the retroperitoneal space). The retroperitoneal space is particularly useful for operations on the aorta and spine.

Minimally invasive surgery has virtually replaced open surgical techniques for operations such as cholecystectomy and anti-reflux surgery of the esophagus and stomach. This has not occurred in either peripheral vascular surgery or cardiovascular surgery. An important type of vascular surgery is to replace or bypass a diseased, occluded, or injured artery. Arterial replacement or bypass grafting has been performed for many years using open surgical techniques and a variety of prosthetic grafts. These grafts are manufactured as fabrics (often from Dacron or Teflon) or are prepared as autografts (from the patient's own tissues) or heterografts (from the tissues of animals). A graft can be joined to the involved artery in a number of different positions, including end-to-end, end-to-side, and side-to-side. This attachment between artery and graft is known as an anastomosis. Constructing an arterial anastomosis is technically challenging for a surgeon in open surgical procedures, and is almost a technical impossibility using minimally invasive techniques.

Minimally invasive surgery is of interest in cardiovascular surgery because of the nature of the tissue of the heart. Cells known as myocytes beat together in unison in a healthy heart when ion channels open and close in an organized manner. Ions pass in and out of the channels, and the change in concentration of ions from within a cell to outside of a cell results in an electrical potential, causing the cell itself to depolarize and repolarize. The depolarization of one cell triggers the cell next to it to depolarize, and thus a cascade effect of depolarization of all the myocytes is triggered and the heart beats. Making several incisions can interrupt this cascade during surgery and change the beating of the heart. Keeping incisions to a minimum with minimally invasive techniques will allow beating heart surgery to be successful while maintaining the electrical integrity of the heart.

Many factors contribute to the difficulty of performing arterial replacement or bypass grafting. See generally, Wylie, Edwin J. et al., Manual of Vascular Surgery, (Springer-Verlag New York), 1980. One such factor is that the tissues to be joined must be precisely aligned with respect to each other to ensure the integrity and patency of the anastomosis. If one of the tissues is affixed too close to its edge, the suture can rip through the tissue and impair both the tissue and the anastomosis. Another factor is that, even after the tissues are properly aligned, it is difficult and time consuming to pass the needle through the tissues, form the knot in the suture material, and ensure that the suture material does not become tangled. These difficulties are exacerbated by the small size of the artery and graft. The arteries subject to peripheral vascular and cardiovascular surgery typically range in diameter from several millimeters to several centimeters. A graft is typically about the same size as the artery to which it is being attached. Another factor contributing to the difficulty of such procedures is the limited time available to complete the procedure. The time the surgeon has to complete an arterial replacement or bypass graft is limited because there is no blood flowing through the artery while the procedure is being done. If blood flow is not promptly restored, sometimes in as little as 30 minutes, the tissue the artery supplies may experience significant damage, or even death (tissue necrosis). In addition, arterial replacement or bypass grafting is made more difficult by the need to accurately place and space many sutures to achieve a permanent hemostatic seal. Precise placement and spacing of sutures are also required to achieve an anastomosis with long-term patency.

Highly trained and experienced surgeons are able to perform arterial replacement and bypass grafting in open surgery using conventional sutures and suturing techniques. A suture has a suture needle that is attached to a long, trailing suture material. The needle must be precisely controlled and accurately placed through both graft and artery. The trailing suture material must be held with proper tension to keep the graft and artery together, and must be carefully manipulated to prevent the suture material from tangling. In open surgery, these maneuvers can usually be accomplished within the necessary time frame, thus avoiding the subsequent tissue damage (or tissue death) that can result from prolonged occlusion of arterial blood flow.

The difficulty of suturing a graft to an artery using minimally invasive surgical techniques has effectively prevented the safe use of this technology in both peripheral vascular and cardiovascular surgical procedures. In some minimally invasive procedures, such as those in the abdominal cavity, the retroperitoneal space, or chest, the space in which the operation is performed is more limited. The exposure to the involved organs is also more restricted than with open surgery. Moreover, in a minimally invasive procedure, the instruments used to assist with the operation are passed into the surgical field through cannulas. When manipulating instruments through cannulas, it is extremely difficult to position tissues in their proper alignment with respect to each other, pass a needle through the tissues, form a knot in the suture material once the tissues are aligned, and prevent the suture material from becoming tangled. Therefore, although there have been isolated reports of vascular anastomoses being formed by minimally invasive surgery, no system has been provided for widespread surgical use that would allow such procedures to be performed safely within the prescribed time limits.

Anastomoses are commonly formed in open surgery by suturing together the tissues to be joined. However, one known system for applying a clip around tissues to be joined in an anastomosis is disclosed in a brochure entitled, "VCS Clip Applier System", published in 1995 by Auto Suture Company, a Division of U.S. Surgical Corporation, wherein a clip is applied by a clip applier about the tissues in a nonpenetrating manner, such that the clip does not penetrate through the tissues, but rather is clamped down around the tissues. It is imperative in forming an anastomosis that tissues to be joined are properly aligned with respect to each other. The clip applier has no means for positioning tissues to ensure proper alignment. Before the clip can be applied, the tissues must first be grasped and properly positioned with respect to each other, for example, by skewering the tissues with a needle as in common suturing techniques, and/or with forceps to bring the tissues together. It is extremely difficult to perform such positioning techniques in minimally invasive procedures within the confines of the cannulas.

Coalescent Surgical, Inc. also produces a U-CLIP Anastomotic Device based on self-closing clip technology of nitinol, which eliminates knot tying. The disadvantage of this system is that the surgeon needs to guide the needle from the graft through the native tissue before the U-CLIP can be deployed to suture the tissue.

Further, when performing mitral valve repairs, it is important to understand that the mitral valve depends on adequate apposition or alignment between the anterior and posterior leaflets along a relatively long surface area under high pressure conditions. Typically, the contact surface is about 12 mm in a direction perpendicular to the anterior-posterior direction and this provides little margin of safety. The leaflet margins are attached to numerous fine chords suspended from attachment points along the inner surface of the left ventricle. Although these attachments are often referred to as papillary muscles, there is often a very diffuse arc-shaped attachment for each of the groups of chords to the endocardial surface. Unfortunately, this anchor point (i.e., the inner wall of the left ventricle) must move with each heartbeat and so the distance between the attachment of the leaflet edges is constantly changing. The chordal lengths may also change, typically increasing with age and degeneration, and the chords frequently do not lengthen in a symmetrical fashion. This leads to variations in the chordal lengths at all-important points of coaptation. Chords may also rupture. In addition, the mitral annulus changes diameter with each heartbeat such that its surface area changes by about 40% with each systole. As the heart enlarges, the annulus of the mitral valve can enlarge as well. In short, there are many variables affecting proper functioning of the mitral valve. The anatomy, such as the leaflet length, the chordal length, and the annular length/diameter, can change. The attachment points can change as the ventricle changes shape. More importantly, all of these aspects can change simultaneously. For example, a patient may have ischemic mitral regurgitation that pulls the posteriolateral valve attachments away from their natural coaptation points and leads to an opening in this area of the mitral valve. This can be further affected if the chordal lengths are changed by even minor degrees of degenerative disease.

Current surgical practice for mitral valve repair generally requires that the mitral valve annulus be reduced in radius by surgically opening the left atrium and then fixing sutures, or more commonly, sutures in combination with a support ring, to the internal surface of the annulus; this structure is used to cinch the annulus, in a purse-string-like fashion, to a smaller radius, thereby reducing mitral regurgitation by improving leaflet coaptation.

This method of mitral valve repair, generally termed "annuloplasty", effectively reduces mitral regurgitation in heart failure patients. This, in turn, reduces symptoms of heart failure, improves quality of life, and increases longevity. Unfortunately, however, the invasive nature of mitral valve surgery and the attendant risks render most heart failure patients poor surgical candidates. Thus, a less invasive means to increase leaflet coaptation and thereby reduce mitral regurgitation in heart failure patients would make this therapy available to a much greater percentage of patients.

Mitral regurgitation also occurs in approximately 20% of patients suffering acute myocardial infarction. In addition, mitral regurgitation is the primary cause of cardiogenic shock in approximately 10% of patients who develop severe hemodynamic instability in the setting of acute myocardial infarction. Patients with mitral regurgitation and cardiogenic shock suffer approximately a 50% hospital mortality. Elimination of mitral regurgitation in these patients would be of significant benefit. Unfortunately, however, patients with acute mitral regurgitation complicating acute myocardial infarction are particularly high-risk surgical candidates, and therefore, are not good candidates for traditional annuloplasty. Thus, a minimally invasive means to effect a temporary reduction or elimination of mitral regurgitation in these critically ill patients would afford them the time to recover from the myocardial infarction or other acute life-threatening events, and make them better candidates for medical interventional or surgical therapy.

It would, therefore, be useful to develop a surgical clip for use in minimally invasive surgeries.

SUMMARY OF THE INVENTION

The present invention provides for a tissue clip for adjoining tissues including a body portion, a biasing mechanism interconnecting the body portion to a tissue grasping mechanism, the grasping mechanism having a first condition wherein the grasping mechanism is extending against and away from the body portion and a second condition wherein the grasping mechanism is biased against the body portion.

The present invention further provides for a combination of the tissue clip of and a deployer, the deployer including a housing having a hollow barrel operatively connected thereto and a handle, the handle having an actuating mechanism for actuating and deploying the tissue clip.

The present invention provides for a combination of the tissue clip having a tongue body portion and a deployer, the deployer including a outer tube having a side slot mechanism for receiving grasping mechanisms of the tissue clip and having an actuating mechanism therein for actuating and deploying the tissue clip.

The present invention also provides for a method of interconnecting tissue, including the steps of deploying the tissue clip, puncturing tissue to be interconnected with the tissue clip, and interconnecting the tissue.

The present invention also provides for a method of treating an aneurism, including the steps of deploying the tissue clip at an aneurism site, closing off the aneurism site with the tissue clip, and treating the aneurism.

The present invention further provides for a method of imaging a surgical procedure with ultrasound, including the steps of modifying a surface of a metal surgical instrument, and imaging the metal surgical instrument with ultrasound during a surgical procedure.

DESCRIPTION OF THE DRAWINGS

Other advantages of the present invention are readily appreciated as the same becomes better understood by reference to the following detailed description, when considered in connection with the accompanying drawings wherein:

FIGS. 1A through F are drawings showing the deployment of two tissue clips of the present invention;

FIGS. 2A through F are drawings showing the deployment of one tissue clip of the present invention;

FIGS. 8A through H are views of the tissue clip of the present invention;

FIGS. 9A through D are views of the tissue clip of the present invention;

FIG. 10 is a representation of the manufacturing of the tissue clip of the present invention;

FIGS. 11A through B are views of the tissue clip of the present invention including coils;

FIGS. 12A through B are views of the tissue clip of the present invention including coils;

FIGS. 13A through C are views of the lock and key mechanism of the tissue clip of the present invention;

FIGS. 49A-49E are representations of a tissue clip with a tongue shaped body;
and
FIGS. 50A and 50B are cross-sectional views of a second embodiment of a tissue clip deployer along its length with a tissue clip inside with a single rod,
and FIGS. 50C and 50D are cross-sectional views of the outer tube of the deployer.

DETAILED DESCRIPTION OF THE INVENTION

Figure 3:
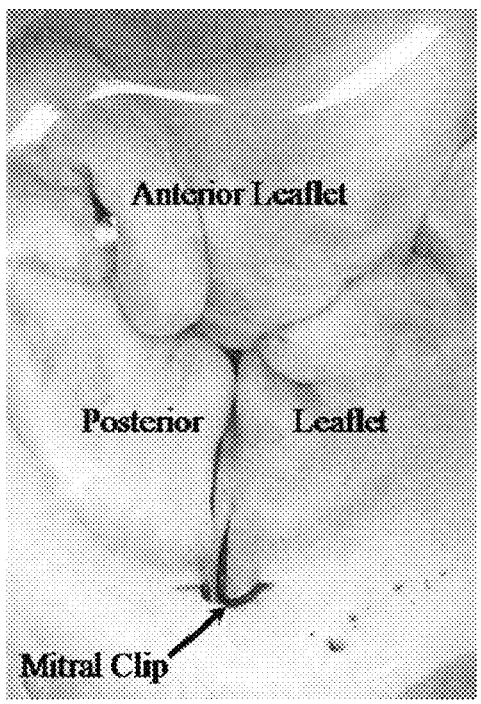
FIG. 3 is an real-time 3-dimensional echocardiography (RT3DE) of a tissue clip of the present invention in use.
Figure 4:
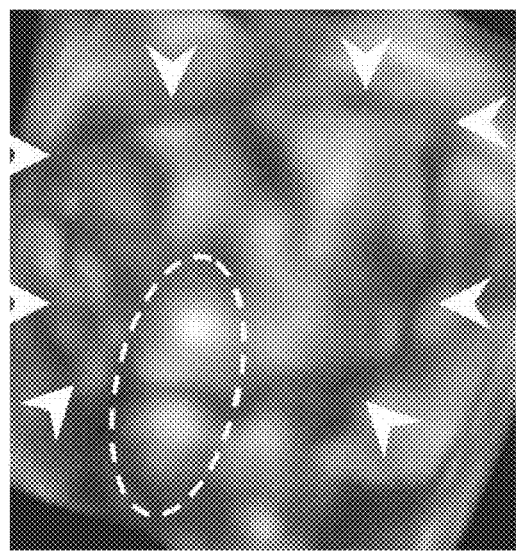
FIG. 4 is a photograph of tissue clip of the present invention in use.

The present invention provides an apparatus for use as a tissue clip. The tissue clip is a clip made of biocompatible materials as generally shown at 10 in the Figures.

The term "tissue clip deployer" and "deployer" both refer to an apparatus used for deploying a tissue clip into tissue. The deployer can be such as one described further herein, or any other suitable deployer can be used, such as a catheter, as long as the deployer allows the tissue clip to function in the manner required for its use.

The term "tissue" as used herein is meant to include, but is not limited to, an aggregation of morphologically similar cells and associated intercellular matter acting together to perform one or more specific functions in the body. Four basic types of tissues include muscle, nerve, epidermal, and connective tissues.

The tissue clip 10 of the present invention has a body portion 16 having at least two arms 12, 14 extending radially therefrom. The arms 12, 14 are biased into position via biasing devices within the body portion 16. The biasing devices can in fact be the material of which the clip is formed. The arms 12, 14 both can include grasping ends 18, 20 to enable the tissue clip 10 to grasp the tissue in need of treatment. Thus, the device 10 will not migrate into the tissue and discomfort to the patient is minimized. The body portion 16 can also be used as a retaining portion. Preferably, the body portion 16 is formed as a single unit with the arms 12, 14; however, the body portion 16 can be a separate piece that is chemically and/or physically attached to the arms 12, 14. The body portion 16 can be of any suitable shape to fit inside or outside the tissue clip deployer and is sized to enable the tissue to be repaired to fit within the body portion 16. The body portion 16 can be a straight line that forms a triangular shape when the arms 12, 14 have grasped and tucked the tissue.

Alternatively, the body portion 16 can be shaped into a loop, circle, triangle, or rectangle. A loop formation, as shown in FIGS. 1-3, enable the clip 10 to more easily be inserted into a deployer. The loop formation also allows the tissue to be grasped like hands and increases contact with tissue to stabilize the tissue clip 10. The arms 12, 14 are less wobbly in this configuration. The body portion 16 can also be shaped as a tongue, as shown in FIGS. 49A-49E, and FIGS. 50A-50D. In this embodiment, it is preferable that the arms 12, 14 remain smooth and do not include the retaining devices described below, allowing the tissue clip 10 to be easily introduced in the tissue to be connected and no additional damage is done when retraction and reposition of the tissue clip 10 is required. Rather, in this embodiment, the tongue body portion 16 includes teeth 17 that help hold the tissue between the arms 12, 14 and the tongue body portion 16. Preferably, the tongue body portion 16 also includes a roughened surface 19. These features of the tongue body portion 16 allow for better visualization during 2D and 3D ultrasound procedures and also prevents the tissue clip 10 from sliding on the tissue being connected. The tissue clip 10 can also include a quadrangular shaped slot 21 on the tongue shaped body portion 16 that can be connected to a rod 28' in deployer 26'. Alternatively, slot 21 can be any other suitable shape to connect with rod 28'.

Varying the size and the position of the arms 12, 14 of the tissue clip 10, affects the amount of tissue that can be tucked into the clip 10. A surgeon can have a set of tissue clips 10 with various sizes of arms 12, 14 for use in various purposes. The angles at which the arms 12, 14 are positioned also affects the amount of tissue that can be clipped. The arms 12, 14 are not so short as to easily dislodge the tissue clip 10 from position; however, the tissue clip 10 can be attached loose enough so that a surgeon can either remove it or reposition it as needed. Each of the portions of the tissue clip 10 can vary in size, material, and flexibility to create different tissue clips 10 for different purposes. Preferably, the tissue clip 10 is of a size relative to the incision in the tissue that is to be closed. Accordingly, the diameter of the arms and the total length of the tissue clip 10 can be selected to fit the incision.

Preferably, the body portion 16 is formed of the same biocompatible material as the arms 12, 14. Alternatively, the body portion 16 can be formed of different biocompatible materials than the arms 12, 14. The body portion 16 can be manufactured separately from the arms 12, 14. The manufacturing can be accomplished using methods known to those of skill in the art.

The grasping ends 18, 20 can be either an integral part of the tissue clip 10, or it can be a separate piece that is physically and/or chemically attached to a first end 22 of the tissue clip 10. The grasping ends 18, 20 preferably include a pointed end portion 24. In one embodiment, the pointed end portion 24 can be in the shape of a fishhook. The fishhook can serve to prevent the tissue clip 10 from migrating backwards, assist in firmly grasping the tissue, and prevent the tissue from becoming unattached. Any other suitable pointed end portion 24 can be used. Examples of such pointed end portions 24 can include barbs, jagged edges, or other tissue clip 10 retaining devices. The end portions 24 can also be beveled. Alternatively, the entire tissue clip 10 can include such barbs, jagged edges, or other retaining devices.

Preferably, the grasping ends 18, 20 are formed from the same biocompatible material as the tissue clip 10. Alternatively, the grasping ends 18, 20 can be formed of a biocompatible material different from the tissue clip 10 in order to enhance its grasping capabilities. The grasping ends 18, 20 can be manufactured separately from the tissue clip 10 if the grasping ends 18, 20 are not an integral part of the tissue clip 10, using methods known to those of skill in the art.

The exterior surface of the tissue clip 10 can be modified in order to enable the tissue clip to perform more effectively. For example, the tissue clip arms 12, 14 can be modified to improve tissue fixation and the arms 12, 14 can be modified to improve visibility by ultrasound and minimize ultrasound artifact and distortion of image. The modifications can be any modification that improves the functionality of the tissue clip 10. Examples of such modifications include, but are not limited to, the addition of hooks, barbs, bristles and bends to the arms 12, 14 of the tissue clip 10 to improve tissue grasping and to increase the force required to remove the anchors. The modifications can be made to improve tissue grasping capabilities and ease of removal. Further examples of surface modifications are described below.

The tissue clip 10 is formed of biocompatible materials. Whenever a foreign object is placed inside the body, rejection reactions can occur ranging from mild to severe irritation and inflammation, to death. To keep rejection minimal, implants must be biocompatible. Preferably, the tissue clip 10 is made of stainless steel. Metals such as stainless steel, shape memory polymers, shape memory alloys, nitinol, titanium alloys, and cobalt alloys have high tensile, fatigue, and yield strengths, low reactivity, and good ductility. A closely packed crystal structure and metallic bonding make metals and alloys useful in internal fixation devices. Alternatively, polymers such as polyethylene (PE) and hydrogels can be used. Depending on the processing methods, polyethylene can be made flexible and elastic, or hard and smooth. Biodegradable polymers can be used in cases where an incision in the tissue is expected to heal and become functional again. These polymers can degrade by hydrolytic instability, hydration, molecular backbone cleavage, loss of molecular weight, and solubilization. The degradation byproducts are removable by the body itself by natural functions such as phagocytosis. Clips of this type eliminate the need for a second operation for removal of the clips. Biodegradable polymers can be natural or synthetic. Some natural polymers include collagen, which already comprises about 30% of the protein in the body; chitosan, which is derived from a polysaccharide called chitin found in crustacean exoskeletons; and polyhydroxyalkanoates (PHA), which are secreted by certain species of microorganisms. Synthetic polymers include poly(glycolic acid) (PGA), which has been used in absorbable sutures; poly(lactic acid) (PLA); copolymers of PGA and PLA; and polydioxananone (PDS). Ceramics and glasses can also be used for the tissue clip 10. Composites of materials can be used to optimize strength and flexibility in the tissue clip 10, and one or more of the materials can be degradable to allow for tissue integration. For example, the tissue clip 10 can be made out of more flexible materials when it is desired to use the tissue clip 10 and subsequently remove it.

In forming the tissue clip 10, the tissue clip 10 can be laser cut (shown generally at 60 in FIG. 10) from a band or cylinder of elastic material. The tissue clip 10 can be laser cut out of a flat sheet of material, especially in the embodiment wherein the body portion 16 is a tongue. The tissue clip 10 can also be formed using heat treatments or other methods known to those of skill in the art.

The tissue clip 10 can also be manufactured using MEMS (Micro-Electric-Mechanical Systems) technology, and include various sensors and electronics to actuate the biasing of the arms 12, 14 or any other portion of the tissue clip 10 as desired. The tissue clip can also include various magnetic portions or electromagnetic portions on both the arms 12, 14 and the body portion 16 that can be actuated to fold the arms 12, 14 of the tissue clip 10 in the desired position.

The tissue clip 10 can also include various coatings described below. These coatings can be on the entire tissue clip 10 or portions thereof. Furthermore, the coatings can be different on the arms 12, 14 than on the body portion 16.

The coating can be used to improve adherence of the tissue clip 10 to tissue. A rougher coating can be used when the tissue clip 10 is desired to remain clipped to tissue (though not so rough as to tear the tissue), whereas a smoother coating can be used when it is desired to remove the tissue clip 10 from tissue. The coating can also induce scar tissue formation or alter the environment surrounding the tissue clip.

The tissue clip 10 can be coated in an immunosuppressible material, or other coating, that limits the ability of the tissue or body within which the tissue clip 10 is being placed to react immunologically to the clip 10. Biologicals or chemicals can be incorporated on the surface of the tissue clip 10 that can be released or directly interact with surrounding tissue to modify tissue reactivity and promote or inhibit cell and extracellular matrix adhesion. Examples of such material include, but are not limited to, immunosuppressive compounds and agents. Immunosuppressive agents are defined as agents that suppress immune responses. The agents can include, but are not limited to, immunoprotective cells such as Sertoli cells, stem cells, stem cell byproducts, or other compounds that create an immunosuppressive effect. Examples of such immunosuppressive compounds include, but are not limited to, PKC inhibitors, glutamate receptor inhibitors, cyclosporins, FK506, corticosteroids, and ascomycins.

The tissue clip 10 can include an imageable material so that the location of the tissue clip 10 in the patient's body can be determined by imaging methods such as ultrasound, magnetic resonance imaging (MRI), computed tomography (CT), X-ray, fluoroscopy, nuclear imaging, or any other imaging method known in the art.

Uncoated metal shows up blurry in ultrasound imaging. Use of a coating therefore allows a surgeon to use ultrasound (such as 3-D real time ultrasound) to determine the position of the tissue clip 10 during surgery. The coating is preferably diffusive and absorptive to improve visibility and reduce artifacts normally produced by uncoated metal. For example, the coating can be polyurethane (such as polyurethane foam) or polytetrafluoroethylene. In addition, a rougher surface of the tissue clip 10 can aid in reducing dampening, as further described below. One advantage of using ultrasound is that it provides a good field image of the tissue clip 10 and area of surgery.

In order for a tissue clip 10 to be imageable in an X-ray visualization procedure, the tissue clip 10 must be more absorptive of the X-rays than the surrounding tissues. Radiopaque materials are commonly used such as stainless steel and nickel-titanium alloys. Radiopaque markers can also be used. In MRI, polymers are typically used. Any other suitable imaging material can be used. The tissue clip 10 can be made of a combination of imageable materials and other biocompatible materials or via a cover 11 formed of an imageable material that is placed about the tissue clip 10. Methods of manufacturing the tissue clip 10 from the materials above are well known in the art.

Figure 47:
FIG. 47 is a photograph of a tissue clip with a surface modification.
Figure 48:
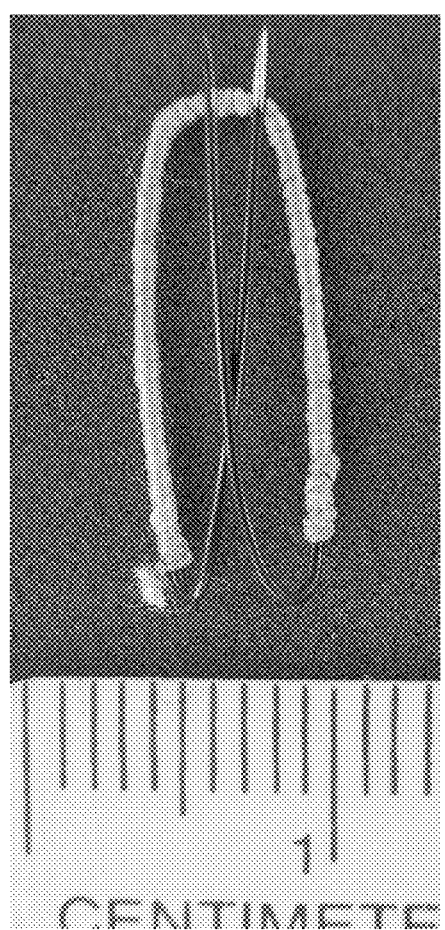
FIG. 48 is a photograph of a tissue clip with a surface modification.

Alternatively, the tissue clip 10 can include physical modifications to better enable the tissue clip 10 to be visualized by any of the visualization methods described above. This is accomplished by providing the best visualization of the arms 12, 14 using ultrasound imaging at all incident angles, which is independent of the direction of the ultrasound beam. The modification also minimizes artifacts formed when the ultrasound beam strikes the arms 12, 14. The modification can be accomplished via diffusive surface modification or coating, examples of which include, but are not limited to, wrapping a wire around the arms 12, 14 or creating channels on the arms 12, 14 to improve visualization. For example, the tissue clip arms 12, 14 can be wrapped in copper wire to improve visualization. FIGS. 47 and 48 show arms 12, 14 wrapped to improve visualization. The same effect can be achieved by cutting grooves, either linear or spiral, into the arms 12, 14. The grooves can be cut using any process known to those of skill in the art. The process can include, but is not limited to, laser or etching. The tissue clip 10 can also include coils 13 made of nitinol, or other similar materials, to aid in the visibility of the tissue clip 10, as shown in FIGS. 11A, 11B, 12A, and 12B. The coils 13 should be coiled loosely enough to enhance the visibility of the tissue clip 10. The surface can also be made smoother via a polyurethane foam coating or other similar compound. Such coating enables easier removal of the tissue clip 10, should removal become necessary.

The tissue clip 10 can also include a lock and key mechanism in order to grab the tissue clip 10 in a stable manner and reposition or remove the tissue clip 10, shown in FIGS. 13A-13C. In this embodiment, the body portion 16 includes locks 58 that fit into key 54 of handle 36 of a deployer (described in detail further below).

The above types of modifications can be combined depending on the needs or circumstances. A combination of modifications can be used in different parts of the same clip.

The tissue clip 10 of the present invention is preferably used to interconnect tissue. For example, the tissue can be heart tissue, muscle tissue, or vascular tissue. Alternatively, the tissue clip 10 can be used to interconnect tissues in any other suitable site in the body. In other words, the tissue clip 10 can be used to clip together any tissue for any purpose of joining tissue together. The tissue clipped can be internal or external. For example, the tissue clip 10 can be used to close a wound instead of using a stapler. The tissue that is being interconnected can be two opposing sides of an incision. It can also be native tissue and graft, or graft tissue and prosthesis. Examples of such interconnections include, but are not limited to, fixation of a patch to tissue for closure of an atrial septal defect, ventricular septal defect, mitral valve repair, orifice or opening into a vessel or aneurysm (out-pouching) in the heart or blood vessel; and/or fixation of two tissue layers together such as two edges of a blood vessel or valve leaflet, vessel to vessel anastomosis, and vessel to synthetic tube graft anastomosis. The tissue clip 10 can also be used to narrow any passageway, such as narrowing a vessel or valve in order to increase pressure within that vessel.

The present invention provides a method of treating an aneurism by deploying the tissue clip at an aneurism site, closing off the aneurism with the tissue clip, and treating the aneurism. The tissue clip effectively creates a wall of tissue that separates the aneurism inside the wall.

The present invention provides a method of joining tissue with the tissue clip 10 by puncturing the tissue of a patient to allow entry of the tissue clip 10 into the tissue. The tissue clip 10 is flushly anchored in the tissue so that the tissue is effectively held together. The method can also include, prior to the puncturing step, a step of deploying the tissue clip 10 through an incision in the tissue in order to suture the tissue. The deploying step is accomplished by inserting a tissue clip deployer into an incision and then guiding the deployer to the site in need of repair. The deployer can also be inserted into a trocar or catheter that is disposed through the incision. A trocar can be used in such operations as a cardiovascular operation. The deployer can be guided to the suture site by using an imaging method such as ultrasound, MRI, CT, X-ray, fluoroscopy, or nuclear imaging.

Prior to entry into the tissue, the arms 12, 14 of the tissue clip 10 are folded as shown in FIGS. 1A and 2A within a deployment device. The tissue clip 10 enters the tissue, and the arms 12, 14, as shown in FIGS. 1D and 2D, open and extend in opposite directions, as shown in FIGS. 1B, 1E, 2B, and 2E. The opening and extending motion enables the arms 12, 14 of the tissue clip 10 to grasp the tissue to be joined. The arms 12, 14 then fold back, or are biased back, on themselves, as shown in FIGS. 1F and 2F, to secure/tuck the tissue to be joined within the tissue clip 10. Thus, the tissue clip 10 functions such that once deployed, it grasps and tucks, within the tissue clip 10, the tissue to be joined.

A deployer 26 is used to store, open, deploy, orient and release the tissue clip 10 into the patient's tissue. In a preferred embodiment, the tissue clip deployer 26 is in the shape of a stapler that includes rods 28, 30 passing therethrough. While the figures show the deployer 26 shaped as a stapler, any other suitable shape can also be used. In general, the deployer 26 is of a small size. The entire deployer 26 or individual parts can be made of any suitable materials such as metals, plastics, ceramics, and composites. The deployer 26 includes a housing 32 having a hollow barrel 34 operatively connected thereto and a handle 36. The handle 36 includes a spring loaded trigger 38. The deployer 26 includes a locking mechanism 40. The locking mechanism 40 is operably connected to an end 41 of the rods 28, 30. The locking mechanism 40 holds the tissue clip 10 that is mounted in the rods 28, 30 and allows the tissue clip 10 to be maintained in the appropriate configuration for deployment. The locking mechanism 40 includes a tip 42 for both holding the tissue clip 10 in place and releasing the tissue clip 10 when positioned at the desired location. The tip 42 can include a hook, gripper, key lock, or other similar design. The tip 42 can be formed from as few as one part or multiple parts 43, 45. When multiple parts 43, 45 are utilized, the parts 43, 45 converge to maintain the tissue clip 10 within an opening 47 in the parts 43, 45. The parts 43, 45 are maintained in a closed position by the rods 28, 30, and sheaths 31, 33 covering the rods 28, 30 of the deployer 26, therefore when the tip 42 is extended from the rods 28, 30 such that the sheaths 31, 33 are no longer covering the parts 43, 45, the parts 43, 45 are no longer held together and the tissue clip 10 can be released. Alternatively, the tip 34 can include a mechanism for locking/closing the parts of the tip 42, which can be released upon deployment of the tissue clip 10.

Figure 5A:
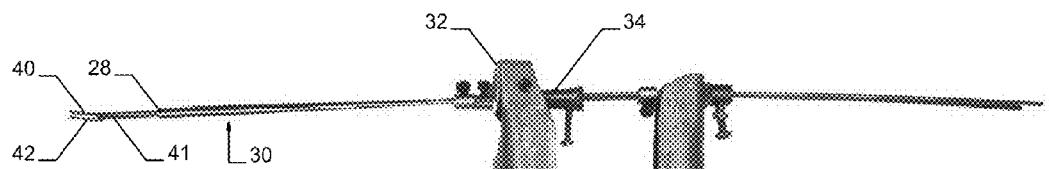
FIGS. 5A and 5C are photographs and 5B a drawing of the tissue clip deployer of the present invention.
Figure 5B:
Figure 5C:
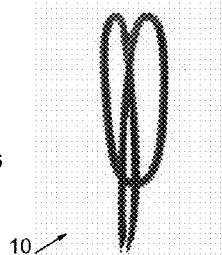
Figure 6A:
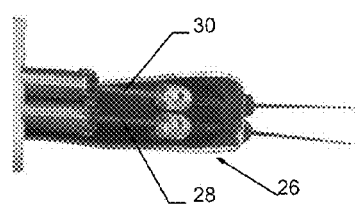
FIGS. 6A through E are photographs of the tissue clip deployer of the present invention.
Figure 6B:
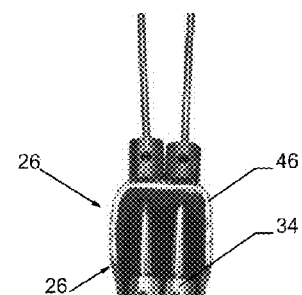
Figure 6C:
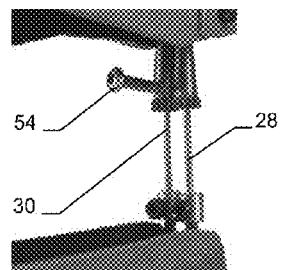
Figure 6D:
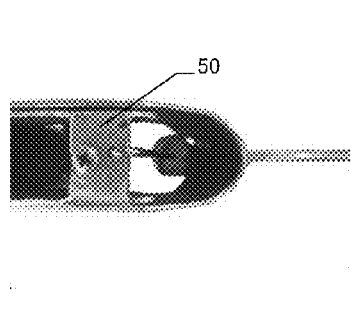
Figure 6E:
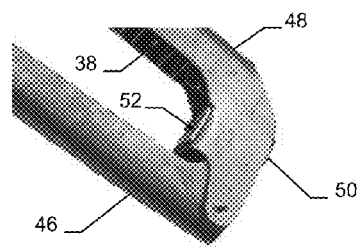
Figure 7A:
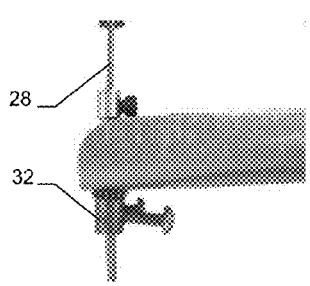
FIGS. 7A through D are photographs of the tissue clip deployer of the present invention.
Figure 7B:
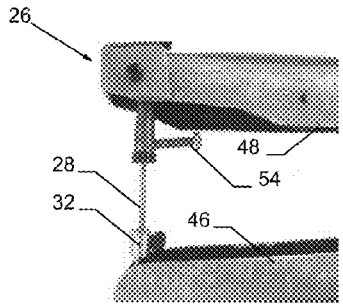
Figure 7C:
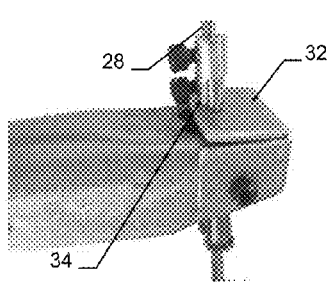
Figure 7D:
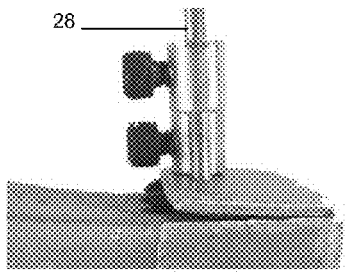
Figure 8A:
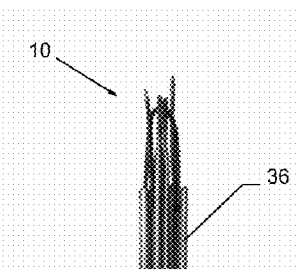
Figure 8B:
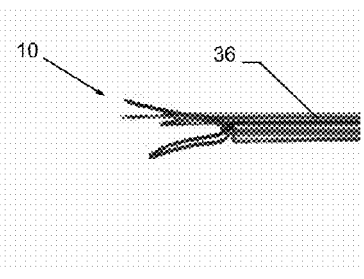
Figure 14A:
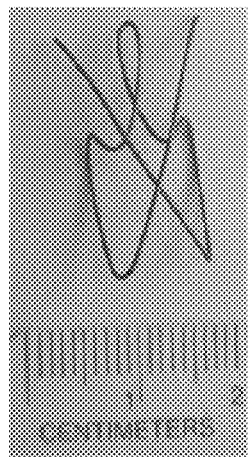
FIGS. 14A through E are photographs of the tissue clip of the present invention: 14A shows tissue clip XX in a right angle, 14B shows tissue clip X in a right angle, 14C shows a tissue clip in a right angle. 14D shows a classic tissue clip in X, 14E shows a classic tissue clip with a 0.5 loop.
Figure 14B:
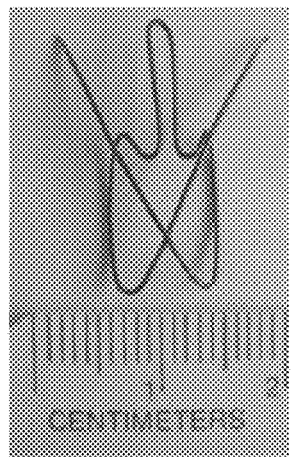
Figure 14C:
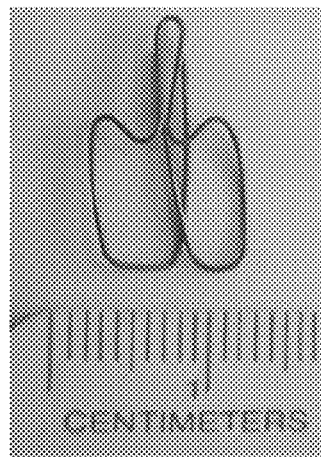
Figure 14D:
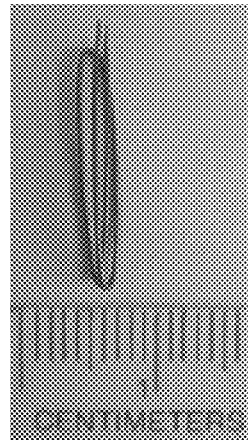
Figure 14E:
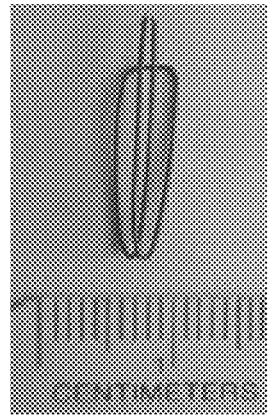
Figure 15:
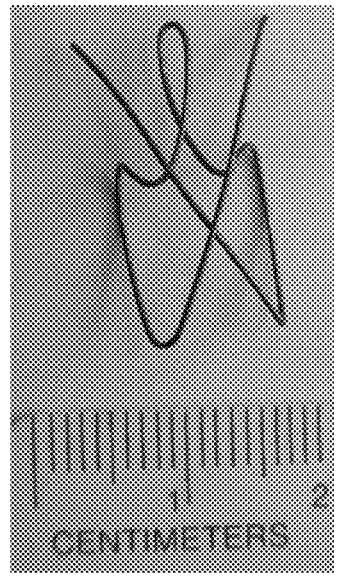
FIG. 15 is a photograph of tissue clip XX.
Figure 16:
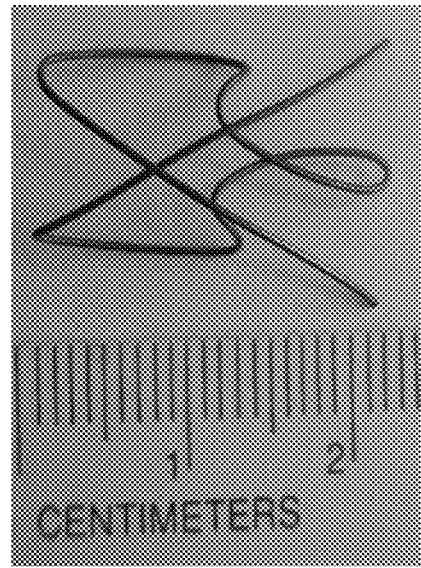
FIG. 16 is a photograph of tissue clip XX.
Figure 17:
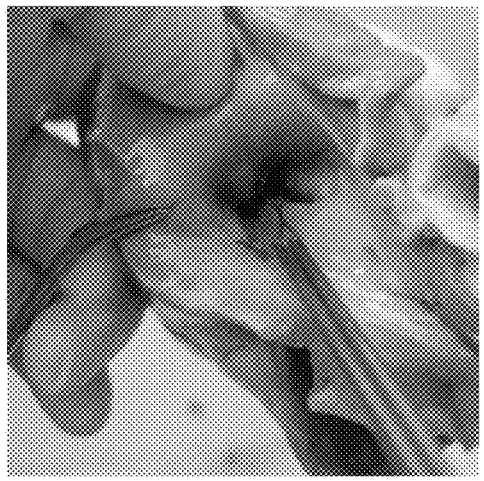
FIG. 17 is a photograph of tissue clip XX.
Figure 18:
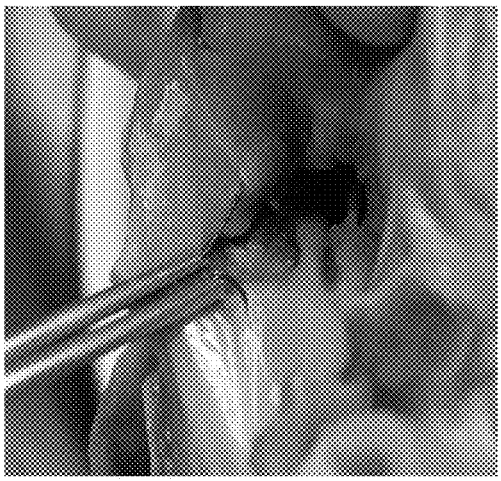
FIG. 18 is a photograph of tissue clip XX.
Figure 19:
FIG. 19 is a photograph of tissue clip XX.
Figure 20:
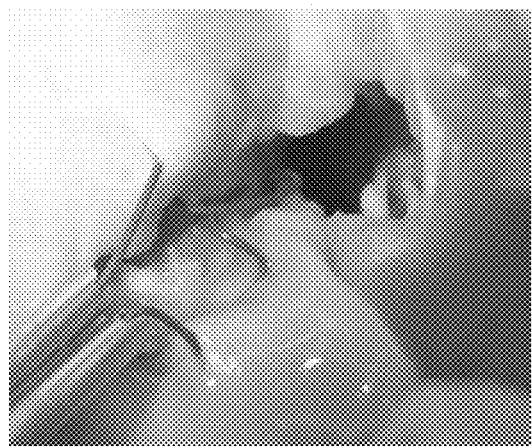
FIG. 20 is a photograph of tissue clip XX.
Figure 21:
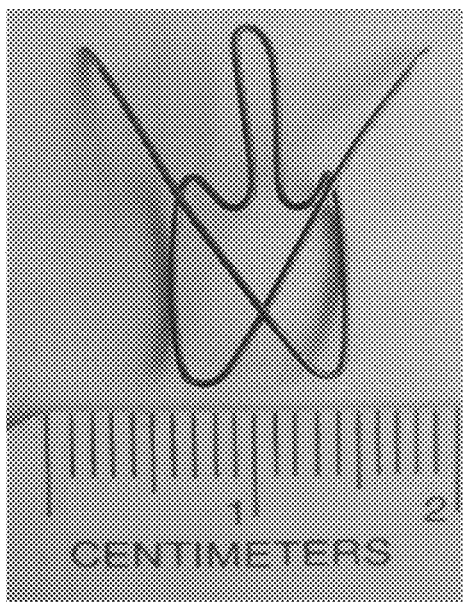
FIG. 21 is a photograph of tissue clip X.
Figure 22:
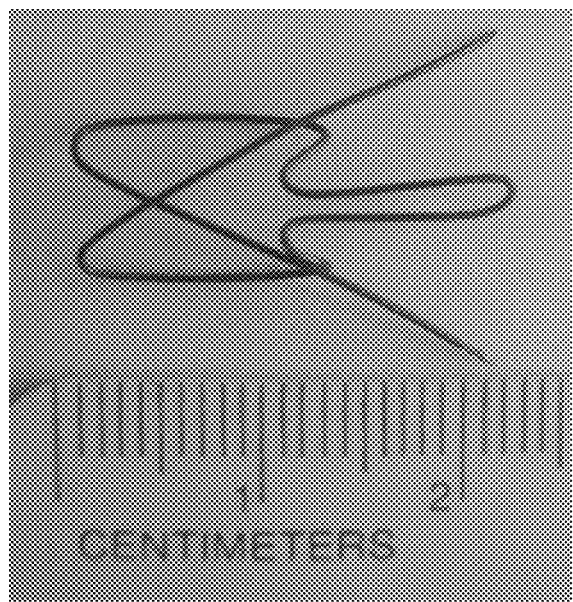
FIG. 22 is a photograph of tissue clip X.
Figure 23:
FIG. 23 is a photograph of tissue clip X.
Figure 24:
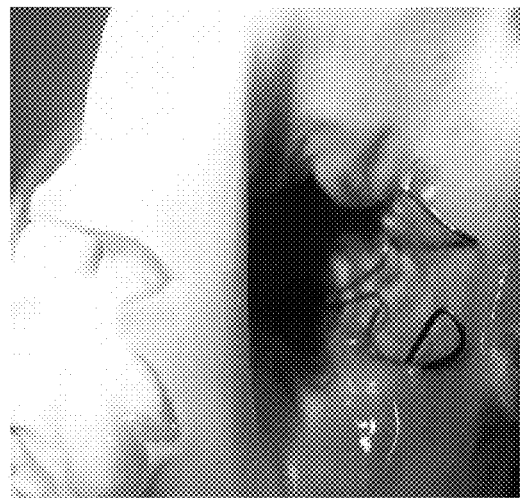
FIG. 24 is a photograph of tissue clip X.
Figure 25:
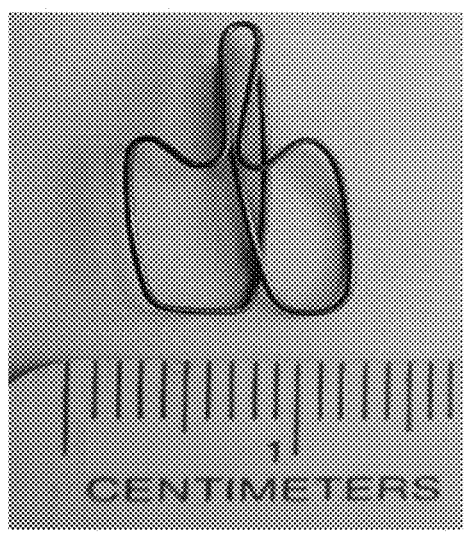
FIG. 25 is a photograph of a tissue clip with a right angle.
Figure 26:
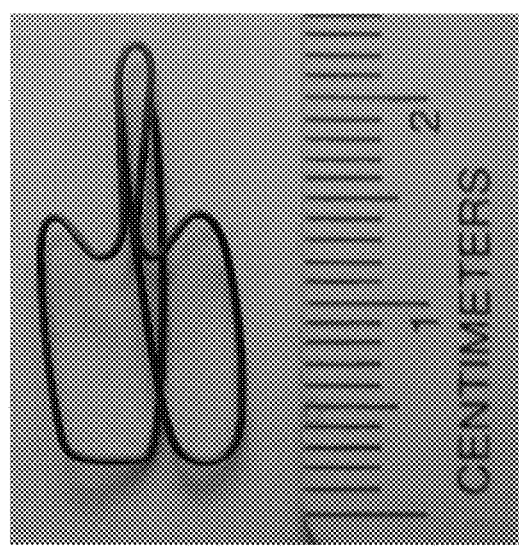
FIG. 26 is a photograph of a tissue clip with a right angle.
Figure 27:
FIG. 27 is a photograph of a tissue clip with a right angle.
Figure 28:
FIG. 28 is a photograph of a tissue clip with a right angle.
Figure 29:
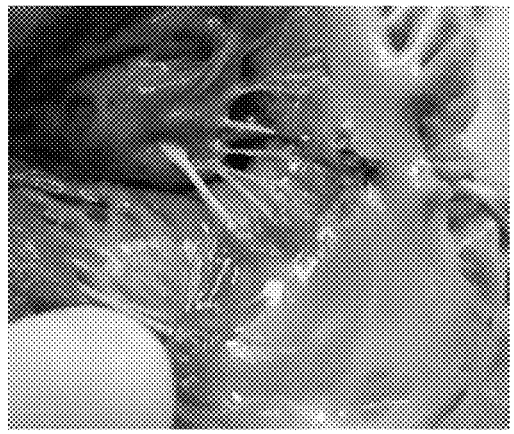
FIG. 29 is a photograph of a tissue clip with a right angle.
Figure 30:
FIG. 30 is a photograph of a tissue clip with a right angle.
Figure 31:
FIG. 31 is a photograph of a classic tissue clip X.
Figure 32:
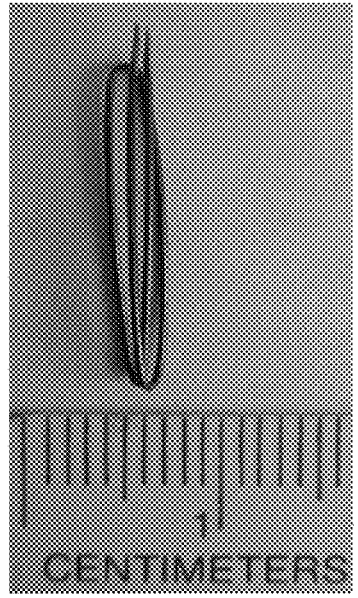
FIG. 32 is a photograph of a classic tissue clip X.
Figure 33:
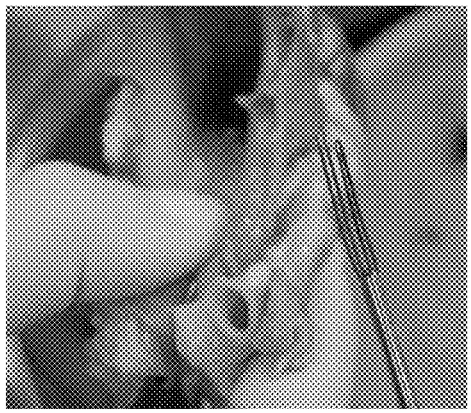
FIG. 33 is a photograph of a classic tissue clip X.
Figure 34:
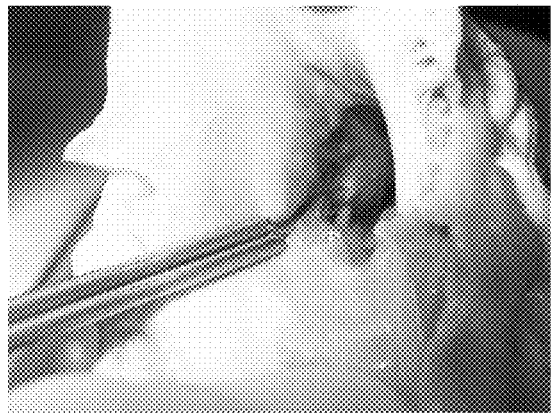
FIG. 34 is a photograph of a classic tissue clip X.
Figure 35:
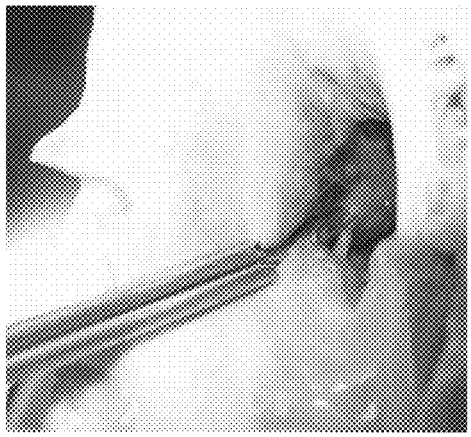
FIG. 35 is a photograph of a classic tissue clip X.
Figure 36:
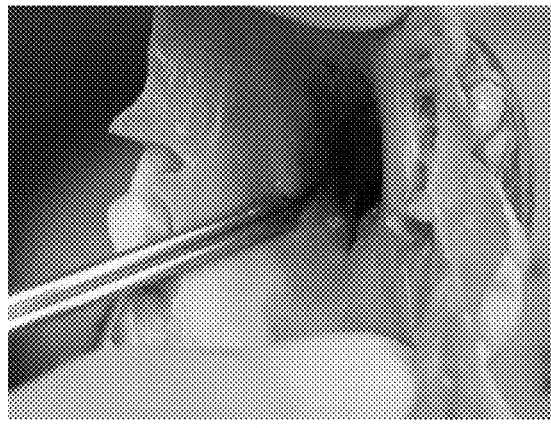
FIG. 36 is a photograph of a classic tissue clip X.
Figure 37:
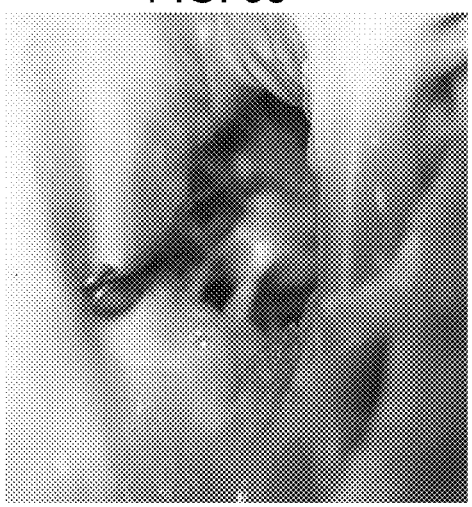
FIG. 37 is a photograph of a classic tissue clip X.
Figure 38:
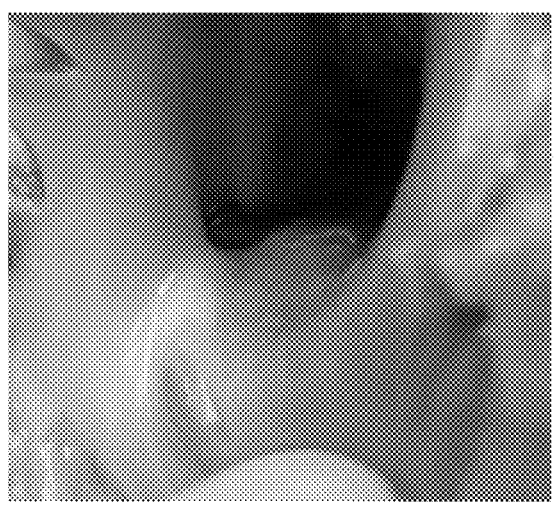
FIG. 38 is a photograph of a classic tissue clip X.
Figure 39:
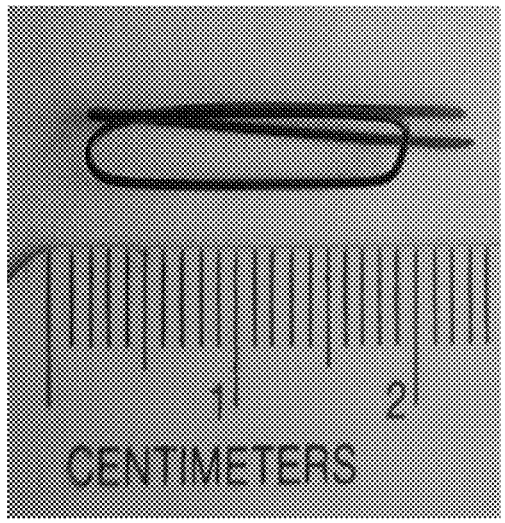
FIG. 39 is a photograph of a classic tissue clip X with a 0.5 loop.
Figure 40:
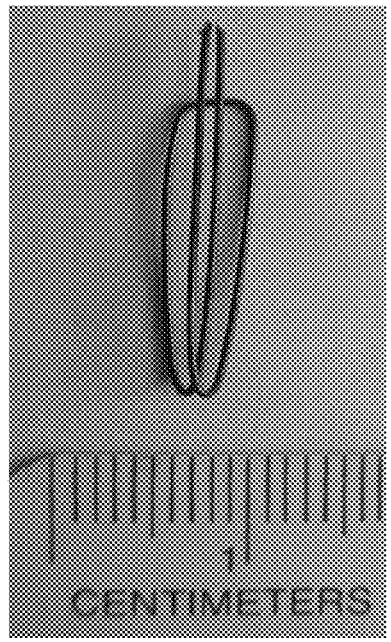
FIG. 40 is a photograph of a classic tissue clip X with a 0.5 loop.
Figure 41:
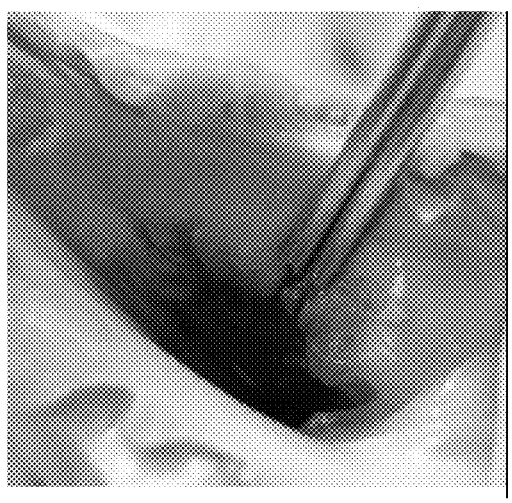
FIG. 41 is a photograph of a classic tissue clip X with a 0.5 loop.
Figure 42:
FIG. 42 is a photograph of a classic tissue clip X with a 0.5 loop.
Figure 43:
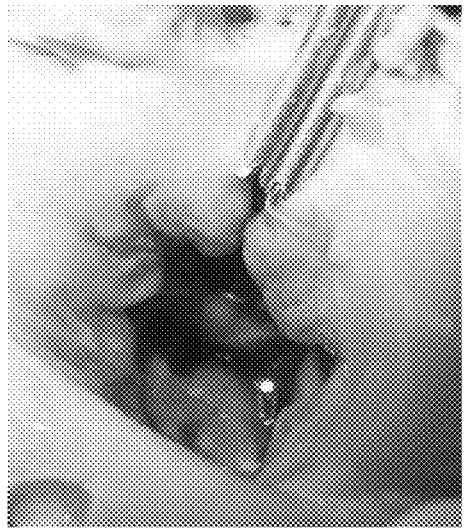
FIG. 43 is a photograph of a classic tissue clip X with a 0.5 loop.
Figure 44:
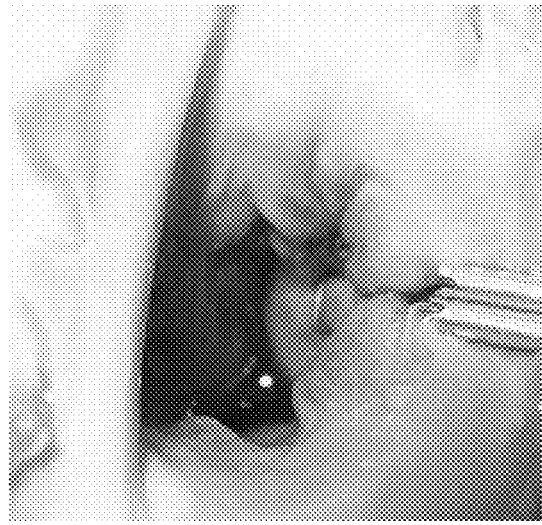
FIG. 44 is a photograph of a classic tissue clip X with a 0.5 loop.
Figure 45:
FIG. 45 is a photograph of a classic tissue clip X with a 0.5 loop.
Figure 46:
FIG. 46 is a photograph of a classic tissue clip X with a 0.5 loop.

The deployer 26 is shown in detail in FIGS. 5-7. The deployer 26 includes a handle 36 that is able to actuate the motion of the tissue clip 10. The handle 36 includes a two arms 46, 48 formed into a V-shape such that the base 50 of the V is distal to the barrel 34 that maintains the rods 28, 30. The two arms 46, 48 of the handle support the rods 28, 30 therebetween. The base 50 of the V contains a hinge 52 that connects the two arms 46, 48 at a pivot point. The handle 36 is actuated by moving the two arms 46, 48 of the handle toward one another. When the two arms 46, 48 are brought into close proximity with one another, such motion causes deployment of the clip 10.

The handle 26 also includes a rod rotation device 54 that rotates the rods 28, 30 into and out of proximity with one another. The rod rotation device 54 is a rotatable device that can be actuated by the user's thumb or other finger. For example, as shown in the Figures, the rod rotation device 54 can be a screw. The rod rotation device 54 turns the rods 28, 30 in order to properly position the clip both within the deployment device 26 and during deployment of the clip 10. This is accomplished because one rod 28 holds the arms 12, 14 of the clip 10 and the second rod 30 holds the body 16 of the clip 10.

In use, the deployer 26 grasps the arms 12, 14 of the clip 10 and stores the clip 10 as shown in FIGS. 8A-8H. The rods 28, 30 are rotated to extend the arms 12, 14 so that the arms 12, 14 can grasp tissue. The twisting of the rods 28, 30 alters the orientation of the clips as shown in FIGS. 1 and 2, and in FIGS. 9A-9D. Once the clip 10 is in the proper position within the patient, the rods 28, 30 are twisted using the rod rotation device 54 to properly position the clip 10, as disclosed herein. In other words, the rods 28, 30 are rotated to close the arms 12, 14 and thus grasp the tissue and fold the arms 12, 14 together. Then the handle 26 is actuated to release the clip 10. Alternatively, the tissue clip 10 automatically folds to its proper position once deployed from the deployer.

In an alternative embodiment, deployer 26' does not require active rotation by the user in order to deploy the tissue clip 10, and is shown in FIGS. 50A-50D. Deployer 26' is a push-pull device such as a tube or syringe instead of a pistol-like device. This type of deployer can be used in surgeries that allow the surgeon to have a second hand free so that both hands can be used to manipulate the deployer. Deployer 26' differs from deployer 26 in that it has only a single rod 28' instead of two rods 28, 30. The deployer 26' includes an outer tube 100 having side slots 102, the outer tube 100 surrounding the rod 28'. Preferably, the tissue clip 10 used with deployer 26' has the tongue for the body portion 16. The tissue clip 10 is attached to the rod 28' at the body portion 16, preferably by the quadrangular slot 21 described above, i.e. a key-hole-like interaction, and arms 12, 14 of the tissue clip 10 sit in the side slots 102. Thus, when the deployer 26' is actuated, the rod 28' pushes the tissue clip 10 and the arms 12, 14 follow the side slots 102 down the outer tube 100, naturally and automatically rotating the arms 12, 14 and grasping the tissue to be connected. There are several advantages of this deployer: a smaller diameter of the overall device can be used since only one rod is required, only one outer tube is required so less parts are required in manufacturing, and the device uses a push-pull motion. The deployer 26' can be made small enough to fit inside a catheter, and one skilled in the art would understand how to use the deployer 26' with a catheter.

The deployer can be used during macrosurgery or microsurgery procedures. The tissue clip 10 rests in a barrel of the deployer prior to deployment into tissue. The diameter of the barrel is such that it can accommodate the diameter of the tissue clip 10. The length of the barrel is such that it can accommodate the length of the tissue clip 10. The length of the barrel can also be extended so that a plurality of tissue clips 10 can be loaded within the deployer. The barrel can also fit though a trocar and cannula if they are used in the operating procedure. In other words, the deployer can be used in a catheter for use of the tissue clip 10 intravascularly or in any other part of the body.

A method of deploying a tissue clip 10 into tissue is provided. This is accomplished by loading a device 10 into the barrel of the deployer, inserting the barrel through an incision of the patient and into the tissue, guiding an end of the barrel to the site to be sutured, and finally driving the device 10 out and off of the barrel and into the tissue at the suture site. Alternatively, instead of one tissue clip 10 loaded into the barrel, a plurality of tissue clips 10 can be loaded. The tissue clips 10 are loaded so that the tissue clips 10 sit inside the barrel, and the arms 12, 14 of the tissue clips 10 project outside of the barrel. Any other suitable method to load the tissue clip 10 can be performed without departing from the spirit of the present invention.

The barrel can be inserted in a trocar disposed in the incision of a patient. The end of the barrel can be imaged while it is in the tissue in order to guide the barrel to the suture site. This can be accomplished by an imaging method such as ultrasound, MRI, CT, X-ray, fluoroscopy, or nuclear imaging. Any other suitable imaging method known to those of skill in the art can also be used. The tissue clip 10 can be driven out and off of the barrel by any other suitable method.

For example, the clip 10 can be deployed under real-time 3-dimensional echocardiography (RT3DE) guidance to the heart from, for example, the left atrium. The arms 12, 14 penetrate the posterior leaflet (PL) at the annulus reaching the ventricular surface as the body portion 16 is simultaneously positioned on the atrial surface of the leaflet. Then, the arms 12, 14 can be rotated toward the body portion 16, folding the prolapsed segment of the PL to create a pleat. The clip 10 can then be disconnected from the deployment device. The results can be visually assessed by the degree of mitral regurgitation.

The tissue clip 10 can be deployed by a surgeon, or alternatively, the tissue clip can be deployed robotically with the use of software. Imaging of the tissue clip 10 can also be controlled robotically.

The present invention is beneficial because the surgeon can perform the procedure in a beating heart and the surgeon can determine how the procedure affects the patient in an objective way. The surgeon can select the number of clips to utilize depending upon where the tissue clip is being inserted. Also, verification can occur to see if the therapy/treatment is working on the heart conduction system. The surgeon is also able to plan and modify the therapy/treatment with opportune information in real time.

The invention is further described in detail by reference to the following experimental examples. These examples are provided for the purpose of illustration only, and are not intended to be limiting unless otherwise specified. Thus, the present invention should in no way be construed as being limited to the following examples, but rather, be construed to encompass any and all variations which become evident as a result of the teaching provided herein.

EXAMPLE 1

Isolated porcine hearts (n=8) were placed into a custom water-filled tank. Left ventricular pressure of 120 mmHg was generated by retrograde flow through the aortic valve. Prolapse of the PL at P2 segment was created by cutting the primary chordae. A clip made of nitinol consists of a loop with two sharpened side arms. The clip was deployed under RT3DE guidance from the left atrium. First, the arms penetrated the PL at the annulus reaching the ventricular surface as the loop was simultaneously positioned on the atrial surface of the leaflet. Then, the arms were rotated toward the loop, folding the prolapsed segment of the PL to create a pleat. The clip was then disconnected from the deployment device. The results were visually assessed by the degree of mitral regurgitation.

The prolapse was successfully eliminated in seven of eight cases. In one case, residual regurgitation was present, and two additional smaller clips were deployed; this reduced the regurgitation but did not eliminate the prolapse completely. Only one clip per procedure was needed in all other cases. The total time per procedure, from introduction of the device to disconnecting the clip, was 7.1±3.8 minutes. No surrounding anatomical structures were compromised.

The above example shows the feasibility of RT3DE-guided mitral valve PL prolapse repair using the clip of the present invention.

EXAMPLE 2

The objective of this experiment was the placement of tissue clips in the mitral ring in order to reduce the diameter of the mitral ring.

Materials and Methods:

The following were used for this experiment: three pieces of porcine or sheep heart (260 grams), scalpel, scissors, camera, gloves, fixation system of the tissue clips (Marco), nitinol tissue clips of 0.45, 1, and 2 cm length (5 units of different models).

Procedure:

Clots were washed and extracted. The mitral valve was identified. Next, the nitinol tissue clips were placed. Puncture was achieved by the system of fixation, to the level of the mitral ring in two points both near commissures. Five different models of Mitral tissue clips were used, cuts were realized in level of one of the commissures, with the intention of increasing the diameter of the ring. Changes concerning reflux were not evaluated.

Results:

Good functioning of the traditional tissue clip is verified (classic tissue clip) (FIGS. 30 to 37). Tissue clip XX, which is crossed in the handle as in the loop with central part in a right angle (90 degrees), does not achieve application adapted even after the second attempt, change is demonstrated in the valvular structure of the previous commissure and in the structure of the tissue clip, it was very unstable (FIGS. 14 to 19).

Tissue clip X, in right angle and crusade only in handles, demonstrates good functioning and manages to close the opening lesion of the mitral orifice, the angle part displaces the ventricular wall towards posterior and the low portion of the loop stays over the papilar muscle (FIGS. 20 to 23).

The tissue clip with a right angle only in the loop, demonstrates good functioning with little injury in segment of the valve, the central portion gets inside the injury and is closed almost completely, equal it is demonstrated loop on muscle papilar, nevertheless in the second attempt, directioning the puncture parallel to ventricular wall, it is able to get over the ventricular wall and does not ride above the mentioned muscle; it is placed in the valve without injury and it diminishes the diameter of the ring (FIGS. 24 to 29). There were not great differences observed with the diameter of the loop (FIGS. 38 to 45).

Observations:

The obtained hearts were very small, the proportion with the tissue clips suggested (of major length) is undesirable due to the fact that they impress too big for the size of the heart. The tissue clips work of with a suitable, better form the thin tissue clips with the center in right angle (90 degrees) and the tissue clip that has alone the crossing in the arms and with the angulation in the loop. The system of fixation has worked in good form, in what concerns obtaining the reconfiguration of the clamp, not so in the liberation since a certain struggle persists in the moment of liberation, which provokes a little protrusion of the clamp. It is demonstrated that the important reduction of the diameter of the valvular ring is accomplished, and approximation in case of an injury to the valve, nevertheless, due to the smallness of the hearts is not achieved to demonstrate the presence of reflux. In case of injury like cleft, the application of the clamp on the injury, in both lips, manages to close it and to return the valvular function. There were realized photographs of the used tissue clips, the procedure and the obtained results as shown in FIGS. 14-46.

Throughout this application, author and year and patents by number reference various publications, including United States patents. Full citations for the publications are listed below.

The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A tissue clip for adjoining tissues, the tissue clip comprising:
a body including at least one elongated body portion having a longitudinal axis, a front, and a back; and
at least two tissue grasping arms each grasping arm comprising an upper portion, an elongated straight portion, and a smooth pointed end portion, wherein the upper portions of the two tissue grasping arms are connected to the body by a biasing mechanism such that the elongated straight portion of each tissue grasping arm is oriented in the same longitudinal direction as the longitudinal axis of the elongated body portion,
wherein the tissue grasping arms have a first condition in which the elongated straight portions of the tissue grasping arms are disposed away from and behind the back of the body and a second condition in which the elongated straight portions of the tissue grasping arms are rotated along their length and towards the front of the body, such that once deployed in tissue, the elongated straight portions of the grasping arms are located in front of the body to both grasp and tuck the tissue to be joined, and wherein when the tissue clip is in the second condition, the elongated straight portions and upper portions of the tissue grasping arms and the elongated body portion form a triangular structure, as viewed from a top or bottom end along the longitudinal axis, with the tissue tucked within the triangular structure.

2. The tissue clip of claim 1, wherein the body is a shape chosen from the group consisting of a straight line, a loop, a circle, a triangle, a rectangle, and a tongue.

3. The tissue clip of claim 1, wherein the tissue clip is formed of a biocompatible material.

4. The tissue clip of claim 3, wherein the biocompatible material comprises one of, or a combination of two or more of, stainless steel, polymers, shape memory polymers, shape memory alloys, nitinol, titanium alloys, and cobalt alloys.

5. The tissue clip of claim 1, wherein the tissue clip is made of a single piece of material and wherein the material comprises the biasing mechanism.

6. The tissue clip of claim 1, wherein the clip is made of at least two pieces of material, such that the at least two tissue grasping arms are attached to the body.

7. The tissue clip of claim 1, wherein the at least two tissue grasping arms include a coating.

8. The tissue clip of claim 7, wherein the coating is an immunosuppressive coating.

9. The tissue clip of claim 8, wherein the immunosuppressive coating comprises one of, or a combination of two or more of, protein kinase C inhibitors, glutamate receptor inhibitors, cyclosporine, FK506, corticosteroids, and ascomycins.

10. The tissue clip of claim 7, wherein the coating is an imageable material.

11. The tissue clip of claim 8, wherein the coating comprises one or both of polyurethane and polytetrafluoroethylene.

12. The tissue clip of claim 1, wherein an exterior surface of the tissue clip includes physical modification.

13. The tissue clip of claim 12, wherein the physical modification is a smooth coating on the tissue grasping arms.

14. A combination comprising:
a tissue clip of claim 1; and
a deployer comprising:
a housing having a hollow barrel operatively connected thereto, and
a handle, the handle comprises an actuator configured for actuating and deploying the tissue clip.

15. The combination of claim 14, wherein the actuator includes a lock for locking and releasing the tissue clip.

16. The combination of claim 14, wherein the actuator comprises:
a first rod for holding the tissue grasping arms of tissue clip,
a second rod for holding the body of tissue clip, and
a rod rotating mechanism for rotating the first rod and the second rod to deploy the tissue clip.

17. A method of performing a mitral valve repair, the method comprising:
deploying a tissue clip, the tissue clip comprising:
a body including at least one elongated body portion having a longitudinal axis, and
at least two tissue grasping arms each grasping arm comprising an upper portion and an elongated straight portion, wherein the upper portions of the at least two tissue grasping arms are connected to the body by a biasing mechanism such that the elongated straight portion of each tissue grasping arm is oriented in the same longitudinal direction as the longitudinal axis of the elongated body portion,
wherein the tissue grasping arms have a first condition in which the elongated straight portions of the tissue grasping arms are disposed away from and behind the back of the body and a second condition in which the elongated straight portions of the tissue grasping arms are rotated about their length and towards the front of the body such that once deployed in tissue, the elongated straight portions of the grasping arms are located in front of the body to both grasp and tuck the tissue to be joined, and wherein when the tissue clip is in the second condition, the elongated straight portions and upper portions of the tissue grasping arms and the elongated body portion form a triangular structure, as viewed from a top or bottom end along the longitudinal axis, with the tissue tucked within the triangular structure;
puncturing mitral valve leaflet tissue to be repaired with each of the grasping arms of the tissue clip and positioning the elongated body portion on an atrial surface of the leaflet; and
rotating the tissue grasping arms along their length towards the elongated body portion in the second condition thereby folding a segment of the leaflet between them to create a pleat within the tissue grasping arms.

18. The method of claim 17, wherein the tissue is repaired with a tissue clip deployer.

19. The method of claim 18, further including folding the tissue grasping arms of the tissue clip into the first condition within the tissue clip deployer prior to deploying the tissue clip.

20. The method of claim 19, wherein the tissue grasping arms are folded automatically.

21. The method of claim 19, wherein the tissue grasping arms are folded manually.

22. The method of claim 17, wherein deploying the tissue clip includes:
  inserting a tissue clip deployer into an incision; and
  guiding the tissue clip deployer to the tissue to be repaired.

23. The method of claim 22, wherein guiding the tissue clip deployer includes imaging the tissue clip deployer.

24. The method of claim 23, wherein imaging the tissue clip deployer includes imaging by a method chosen from ultrasound, real time 3D echocardiography, MRI, CT, X-ray, fluoroscopy, and nuclear imaging.

25. The method of claim 17, wherein the tissue clip is deployed through a catheter.

26. A method of treating an aneurism, the method including:
  deploying the tissue clip of claim 1 at an aneurism site;
  closing off the aneurism site with the tissue clip; and
  treating the aneurism.

27. The method of claim 26, wherein closing off the aneurism site includes:
  creating a wall of tissue; and
  separating the aneurism inside the tissue.

28. The method of claim 17, wherein the method is used for mitral valve posterior leaflet prolapse repair.

29. The method of claim 17, further comprising rotating the tissue grasping arms along their length away from the elongated body portion to return the tissue clip to the first condition thereby releasing the segment of the leaflet between them to enable removal and repositioning of the tissue clip at another location of the leaflet.

* * * * *

UNITED STATES PATENT AND TRADEMARK OFFICE
CERTIFICATE OF CORRECTION

PATENT NO. : 9,307,984 B2  Page 1 of 1
APPLICATION NO. : 12/936992
DATED : April 12, 2016
INVENTOR(S) : del Nido et al.

It is certified that error appears in the above-identified patent and that said Letters Patent is hereby corrected as shown below:

In the claims

Col. 15, line 61, Claim 9, delete "cyclosporine," and insert -- cyclosporins, --, therefor.

Signed and Sealed this
Twenty-eighth Day of June, 2016

Michelle K. Lee
*Director of the United States Patent and Trademark Office*